United States Patent
Lebner (10) Patent No.: US 12,059,324 B2
(45) Date of Patent: *Aug. 13, 2024

(54) POLYMERIC FILM DISONTINUITIES IN WOUND CLOSURE DEVICE

(71) Applicant: ClozeX Medical, Inc., Wellesley Hills, MA (US)

(72) Inventor: Michael Lebner, Wellesley Hills, MA (US)

(73) Assignee: ClozeX Medical, Inc., Wellesley Hills, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/163,088

(22) Filed: Feb. 1, 2023

(65) Prior Publication Data

US 2023/0172760 A1 Jun. 8, 2023

Related U.S. Application Data

(63) Continuation of application No. 16/826,719, filed on Mar. 23, 2020, now Pat. No. 11,576,820.

(60) Provisional application No. 62/832,965, filed on Apr. 12, 2019.

(51) Int. Cl.
| | | |
|---|---|---|
| *A61F 13/0246* | (2024.01) | |
| *A61B 17/08* | (2006.01) | |
| *A61F 13/00* | (2024.01) | |
| *A61F 13/02* | (2024.01) | |

(52) U.S. Cl.
CPC ........ *A61F 13/0253* (2013.01); *A61B 17/085* (2013.01); *A61F 13/0236* (2013.01); *A61F 13/0259* (2013.01); *A61B 2017/086* (2013.01); *A61F 2013/00336* (2013.01)

(58) Field of Classification Search
CPC .... A61F 5/443; A61F 13/025; A61F 13/0233; A61F 13/0236; A61F 13/0243; A61F 13/0246; A61F 13/0253; A61F 13/0259; A61F 13/00085; A61F 2013/00246; A61F 2013/00251; A61F 2013/00255; A61F 2013/00259; A61F 2013/00336; A61F 2013/00582; A61F 13/024; A61B 17/04;
(Continued)

(56) References Cited

U.S. PATENT DOCUMENTS

| | | |
|---|---|---|
| 6,329,564 B1 | 12/2001 | Lebner |
| 6,822,133 B2 | 11/2004 | Lebner |
| 6,831,205 B2 | 12/2004 | Lebner |

(Continued)

FOREIGN PATENT DOCUMENTS

| | | |
|---|---|---|
| WO | 2018085795 A1 | 5/2018 |
| WO | 2019183419 A1 | 9/2019 |

*Primary Examiner* — Ophelia A Hawthorne
*Assistant Examiner* — Gina McCarthy
(74) *Attorney, Agent, or Firm* — Pierce Atwood LLP; Christopher A. Baxter (57) ABSTRACT

The present disclosure relates to a two-component medical device for closing a wound or incision. The two-component device comprising a first and second component, each comprising an adhesive-backed anchoring member having one edge referred to as the wound edge. The adhesive-backed anchoring members are produced from a polymeric film sheet. Disclosed are instances wherein the adhesive-backed anchoring members are characterized by the presence of one or more discontinuities in the polymeric film sheet.

9 Claims, 2 Drawing Sheets (58) Field of Classification Search
CPC ... A61B 17/0466; A61B 17/08; A61B 17/085; A61B 2017/081; A61B 2017/086
See application file for complete search history.

(56) References Cited

U.S. PATENT DOCUMENTS

| | | |
|---|---|---|
| 7,332,641 B2 | 2/2008 | Lebner |
| 7,354,446 B2 | 4/2008 | Lebner |
| 7,414,168 B2 | 8/2008 | Lebner |
| 7,511,185 B2 | 3/2009 | Lebner |
| 7,563,941 B2 | 7/2009 | Lebner et al. |
| 7,838,718 B2 | 11/2010 | Lebner |
| 8,636,763 B2 | 1/2014 | Lebner |
| 2002/0099315 A1 | 7/2002 | Lebner |
| 2005/0020957 A1* | 1/2005 | Lebner ................ A61B 17/085 602/42 |
| 2005/0240221 A1 | 10/2005 | Dunshee |
| 2005/0284801 A1 | 12/2005 | Tacklind |
| 2006/0009099 A1 | 1/2006 | Jonn et al. |
| 2009/0036922 A1 | 2/2009 | Riskin et al. |
| 2013/0152945 A1 | 6/2013 | Locke et al. |
| 2014/0058444 A1 | 2/2014 | Fox |
| 2015/0133844 A1* | 5/2015 | Montulet ............ A61F 13/0259 602/44 |
| 2016/0317358 A1* | 11/2016 | Holm .................... A61F 13/024 |
| 2018/0193019 A1 | 7/2018 | Yang et al. |
| 2020/0146899 A1 | 5/2020 | Pratt et al. |
| 2021/0113208 A1* | 4/2021 | Varadarajan ........ A61F 13/0236 |

* cited by examiner

POLYMERIC FILM DISONTINUITIES IN WOUND CLOSURE DEVICE

RELATED APPLICATIONS

The present application is a continuation of U.S. Nonprovisional application Ser. No. 16/826,719 filed on Mar. 23, 2020, which claims the benefit under 35 U.S.C. § 119(e) of U.S. Provisional Application No. 62/832,965 filed Apr. 12, 2019, the contents of which are incorporated by reference in their entirety.

BACKGROUND

A number of United States patents have issued naming inventor Michael Lebner and directed toward a two-component medical device for closing a wound or incision, or methods related to same. Examples of such patents include U.S. Pat. Nos. 6,329,564; 6,831,205; 6,822,133; 7,511,185; 8,636,763; 7,414,168; 7,332,641; 7,354,446; 8,636,763; 7,838,718; 7,414,168 and 7,563,941, the disclosures of which are incorporated herein by reference. A common feature of these two component wound closure devices are a pair of (i.e., a first and a second) adhesive-backed anchoring members that are adhered to the skin on opposite sides of the wound or incision to be closed. Each of the first and second adhesive-backed anchoring members comprise an edge, referred to as a wound edge, to be applied generally parallel and adjacent to the wound to be closed.

Adherence of the first and second adhesive-backed anchoring members to the skin can present challenges, in particular, when applied to a physically active user. The build-up of sweat under the adhesive-backed anchoring members, particularly in combination with repeated joint flexion can tend to cause unintended release of an adhesive-backed anchoring member.

SUMMARY

The present disclosure relates to a two-component medical device for closing a wound or incision. The two-component device comprising a first component comprising: a) a first adhesive-backed anchoring member having one edge referred to as the wound edge of the first adhesive-backed anchoring member, wherein the first adhesive-backed anchoring member is produced from a polymeric film sheet and wherein the first adhesive-backed anchoring member is characterized by the presence of one or more discontinuities in the polymeric film sheet allowing for the release of sweat from beneath the first adhesive-backed anchoring member; ii) one or more first elongated connectors extending from the wound edge of the first adhesive-backed anchoring member; and iii) one or more first pulling elements joined to the one or more first elongated connectors and adapted for translation of the first adhesive-backed anchoring member toward a wound or incision; and b) a second component comprising: i) a second adhesive-backed anchoring member having one edge referred to as the wound edge of the second adhesive-backed anchoring member, wherein the second adhesive-backed anchoring member is produced from a polymeric film sheet and wherein the second adhesive-backed anchoring member is characterized by the presence of one or more discontinuities in the polymeric film sheet allowing for the release of sweat from beneath the first adhesive-backed anchoring member; ii) one or more second elongated connectors extending from the wound edge of the second adhesive-backed anchoring member; and iii) one or more second pulling elements joined to the one or more second elongated connectors and adapted for translation of the second adhesive-backed anchoring member toward the wound or incision; c) one or more release liners protecting the adhesive-backed surfaces of the first adhesive-backed anchoring member and the second adhesive-backed anchoring member; d) means for attaching the one or more first elongated connectors to the second adhesive-backed anchoring member thereby forming an attached portion and a bridging portion for each attached first elongated connector; and e) means for attaching the one or more second elongated connectors to the first adhesive-backed anchoring member thereby forming an attached portion and a bridging portion for each attached second elongated connector.

In embodiments, the disclosure relates to the two-component medical device as described above wherein the one or more discontinuities comprise one or more slices. In embodiments, the slices are perpendicular to the wound edge. In embodiments, the slices perpendicular to the wound edge are in a portion of the first or second adhesive-backed anchoring members that are not covered by elongated connectors when the device is applied. In embodiments of the two-component medical device disclosed, the one or more discontinuities comprise one or more perforations.

In embodiments of the two-component medical device disclosed, the first and second adhesive-backed anchoring members are produced from transparent stock. In embodiments, the first and second adhesive-backed anchoring members are produced from inelastic stock, or from elastic stock reinforced with an inelastic structural material. In embodiments, the first and second adhesive-backed anchoring members are produced from a vapor-permeable stock. In embodiments, the pulling elements and/or anchoring members are coded to enable user distinction. In instances of the two-component medical device disclosed, the coding comprises an observable geometric distinction. In embodiments of the two-component medical device disclosed, the coding comprises printed indicia. In embodiments of the two-component medical device disclosed, the coding comprises distinguishing colors.

In embodiments of the two-component medical device disclosed, pulling elements are removable following application of the device. In instances of the two-component medical device disclosed, the pulling elements are reinforced with a pull bar.

In embodiments of the two-component medical device disclosed, the means for attaching the one or more first and second elongated connectors to the second and first adhesive-backed anchoring member during closure comprises adhesive. In instances of the two-component medical device disclosed, the adhesive is provided on the lower surfaces of the first and second elongated connectors.

In embodiments of the two-component medical device disclosed, the release liners are optionally coded to indicate sequence of removal. In instances of the two-component medical device disclosed, the coding comprises printed indicia enabling user distinction between the first and second release liner. In embodiments of the two-component medical device disclosed, the coding comprises distinguishing colors between the first release liner and the second release liner. In embodiments of the two-component medical device disclosed, the first and second adhesive-backed anchoring members are provided with one or more alignment indicators. In instances of the two-component medical device disclosed, the first and second adhesive-backed anchoring members are provided with a wound edge bar. In embodiments of the two-component medical device disclosed, the edges of the first and second adhesive-backed anchoring members adjacent the wound or incision are curved or angled to evert the skin edges.

In embodiments of the two-component medical device disclosed, a portion of the first and second elongated connectors is cut away to increase unobstructed surface area above the wound or incision thereby facilitating drainage of exudates and application of medication. In embodiments of the two-component medical device disclosed, the elongated connectors are sufficiently spaced-apart to facilitate lateral adjustment of the first elongated component relative to the second elongated component. In embodiments of the two-component medical device disclosed, the first and second adhesive-backed anchoring members are produced from an elastic polymeric material not reinforced with an inelastic structural material.

In embodiments of the two-component medical device disclosed, the first and second adhesive-backed anchoring members are made from inelastic material that is altered by mechanical manipulation thereby providing the altered first and second anchoring members with elastic properties. In embodiments of the two-component medical device disclosed, the first and second elongated connectors are strap-like such that the width of each is greater than the thickness of each. In instances of the two-component medical device disclosed, the attachment of the first and second elongated connectors to the second and first adhesive-backed anchoring members forms an attached portion and a bridging portion for each individual elongated connector, wherein the average width of the bridging portion of each elongated connector is less than the average width of the attached portion. In embodiments of the two-component medical device disclosed, the bridging portions are substantially free of adhesive. In embodiments of the two-component medical device disclosed, the first and second adhesive-backed anchoring members are perforated in a direction generally perpendicular to their respective wound edges thereby facilitating removal of a portion of the device thereby reducing the size of the device or creating multiple devices.

In instances of the two-component medical device disclosed, the device contains embedded infection indicators useful for detecting the development of infection. In embodiments of the two-component medical device disclosed, the device is adapted for transdermal drug delivery. In embodiments of the two-component medical device disclosed, the device comprises an elastic tension indicator element. In instances of the two-component medical device disclosed, the one or more discontinuities comprise one or more punches. In embodiments of the two-component medical device disclosed, the first elongated component and the second elongated component, or elements thereof, are die cut from sheet stock. In embodiments of the two-component medical device disclosed, the first and second elongated components are interlaced. In embodiments of the two-component medical device disclosed, the first and second elongated components are mated in a keyhole arrangement. In embodiments of the two-component medical device disclosed, the width of the attached portions is constant.

In embodiments of the two-component medical device disclosed, at least the first and second adhesive-backed anchoring members are produced from colored or opaque stock. In embodiments of the two-component medical device disclosed, the discontinuities increase breathability of the material. In embodiments of the two-component medical device disclosed, the discontinuities facilitate transfer of sweat from the skin beneath the first and second adhesive-backed anchoring members when in use. In embodiments of the two-component medical device disclosed, the discontinuities results in elastic-like properties. In embodiments of the two-component medical device disclosed, the discontinuities are invisible to a user. In embodiments of the two-component medical device disclosed, the slices in adhesive-backed anchoring members create a plurality of adhering subdomains.

DETAILED DESCRIPTION

The present disclosure relates to a two-component medical device useful for closing a wound or incision. Embodiments of the two-component medical device include a first component including a first adhesive-backed anchoring member having one edge referred to as a wound edge of the first adhesive-backed anchoring member. The first component also includes one or more first elongated connectors extending from the wound edge of the first adhesive-backed anchoring member and one or more first pulling elements joined to the one or more first elongated connectors and adapted for translation of the first adhesive-backed anchoring member toward a wound or incision.

Embodiments also include a second component including a second adhesive-backed anchoring member having one edge referred to as a wound edge of the second adhesive-backed anchoring member. The second component also includes one or more second elongated connectors extending from the wound edge of the second adhesive-backed anchoring member and one or more second pulling elements joined to the one or more second elongated connectors and adapted for translation of the second adhesive-backed anchoring member toward the wound or incision.

Embodiments also include one or more release liners protecting the adhesive-backed surface of the first adhesive-backed anchoring member. Each release liner protecting the adhesive-backed surface of the first adhesive-backed anchoring member preferably includes a tab portion for removal.

Embodiments further include one or more release liners protecting the adhesive-backed surface of the second adhesive-backed anchoring member. Each release liner protecting the adhesive-backed surface of the second adhesive-backed anchoring member preferably includes a tab portion for removal.

Means are provided for attaching the one or more first elongated connectors to the second adhesive-backed anchoring member thereby forming an attached portion and a bridging portion for each attached first elongated connector. Means are also provided for attaching the one or more second elongated connectors to the first adhesive-backed anchoring member thereby forming an attached portion and a bridging portion for each attached second elongated connector.

As discussed in the Background section, adhesive-backed anchoring members of a two-component medical device can lose adherent properties through the build-up of sweat beneath the adhesive-backed anchoring members. This loss of adhesion can become critically important when the medical device is placed on an athlete and subjected to excessive sweating, or on a joint, such as a knee or shoulder, and subjected to stretching and rotational movements. The present disclosure relates to the introduction of discontinuities in adhesive-backed anchoring members of a two-component medical device thereby allowing for the release of sweat from beneath the first and second adhesive-backed anchoring members. Prior to describing instances of discontinuities in detail, certain other consideration that may relate to instances of the disclosure will be discussed.

Interlaced and Keyhole Embodiments

Embodiments of the medical device of the present disclosure can be interlaced or non-interlaced. Interlaced embodiments are those wherein both the first and second components comprise two or more elongated connectors, wherein the first and second elongated connectors of the first component are attached to a single pulling element and the first and second elongated connectors of the second component are attached to another single pulling element. Further, an elongated connector from one of the two components passes through the void formed between the two elongated connectors of the other component. When assembled in this manner, the first and second components are linked and they cannot be separated without cutting or breaking at least one of the two components. A simple analogy to such an interlaced device is a pair of interlocking rings.

One of skill in the art will recognize that more complex interlaced embodiments can be produced wherein, referring to a first component, interlacing extends to two or more adjacent voids formed by three or more adjacent elongated connectors. Examples of such embodiments are provided in the disclosures in issued US patents referenced and incorporated by reference in the Background section.

Interlaced embodiments can be produced in a variety of ways. Consider, for example, the simplest embodiment to which the analogy to interlocking rings has been made. To produce such an interlaced structure, the first and second components can be die cut as monolithic elements. One of the two components can then be cut, interlaced with the uncut component, and the cut can then be repaired, for example, with adhesive or some other appropriate means. As an alternative method for producing the simplest interlaced embodiment, one component can be die cut monolithically, and the second component can be die cut with an element, or a portion of an element missing. For example, the second component could be die cut with one of the two required elongated connectors being absent. The missing second elongated connector could be provided as a separate die cut element, complete with adhesive. Following interlacing of the first component with the partial second component, the interlaced structure could be completed by attaching the separately supplied missing elongated connector.

Neither of the interlaced device production methods discussed above is adaptable to a computer-controlled, mass production, manufacturing technique. Such methods have, however, been developed, publicly disclosed and incorporated herein by reference. Given this disclosure, one of skill in the art can develop and implement computer-controlled methods for production of interlaced embodiments of the two component medical device of the present disclosure.

A non-interlaced alternative design has been referred to as the "key-hole" design. In this design, for example, the two components of the two-component medical device are separately produced. In a preferred method, they are produced through a die cut process as monolithic components. Each of the two monolithic components comprise a adhesive-backed anchoring member, elongated connector(s) and a pulling element. The elongated connector(s) of the first component are centrally located in the assembled and applied device. The elongated connectors of the second component are spaced apart thereby creating a void, or "key-hole" through which the pulling element and elongated connector(s) of the first element are inserted. Following insertion and rotation of the first and second components into a common plane, the two components are mated in a "key-hole" arrangement and the two-component device is in condition for application.

Sheet Stock

In preferred embodiments, the adhesive-backed anchoring members, elongated connectors and pulling elements are produced from a substantially inelastic polymeric material. Alternatively, they may be produced from an elastic material which is reinforced with an inelastic structural component thereby rendering the device substantially inelastic. For example, such inelastic materials may include monofilament polymeric line or mesh. Such reinforced polymers are referred to herein as polymeric composites. A reinforcing, inelastic structural material is referred to in the art as "scrim". Scrim may be a woven textile or polymer, a non-woven polymer, or any other structural material that acts to stabilize the substrate. Preferably, the scrim reinforced substrate will have a high degree of permeability (e.g., 1,000 to 8,000 liters/sec/m$^2$).

Additionally, non-reinforced polymers exhibiting a degree of elasticity (e.g., polyurethane or polyester) may be used in the production of adhesive-backed anchoring members for embodiments in which adhesive-backed anchoring members and elongated connectors are produced separately, and subsequently attached to one another (i.e., non-monolithic embodiments). A preferred polymer for the production of the adhesive-backed anchoring members is polyurethane having a thickness of 3-12 mils. Such a polymer is breathable and exhibits a degree of flexibility. If a non-reinforced elastic polymer is used to produce an adhesive-backed anchoring member, it will be preferable to reinforce the upper surface of the wound edge with an inelastic element so that the wound edge remains substantially straight across the incision site during the closure process. Such an element is referred to herein as a "wound edge bar". One skilled in the art will recognize that a wide range of inelastic polymers, or even metals, can be utilized in the production of a wound edge bar for the purpose of providing rigidity to the wound edge. Vapor permeable polymeric materials that satisfy the other requirements for use in the manufacturing of the device offer improved comfort and are preferred. Transparent stock is also preferred so that the healing process and the entire wound site can be monitored easily. Therefore, at least the first and second adhesive-backed anchoring members are produced from transparent stock in preferred embodiments. As an alternative design choice, colored or opaque stock may be used in the production of at least the first and second adhesive-backed anchoring members when circumstances (e.g., cost considerations) dictate.

In preferred embodiments, the adhesive-backed anchoring members, elongated connectors and pulling elements are produced from sheets or rolls of polymeric material or polymeric composite material (e.g., polyurethane or polyester). The sheet or roll stock is typically referred to as "film" as the thickness in preferred embodiments ranges from about 0.5 mil to about 5 mil, and may vary depending upon application. Die cutting these elements from polymeric sheet stock to provide two monolithic components (i.e., having no seams or joints) which, when assembled/packaged comprise the two-component device, is a particularly cost-effective approach to manufacturing. Die cutting can be combined with other assembly steps, for example, in connection with the production of interlaced embodiments as discussed elsewhere herein. Laser and ultrasonic trimming devices are also examples of equipment that can be used to cut the components of the present disclosure. The sheet stock may be perforated to allow for the exchange of air with the skin beneath the two-component device.

Application Considerations

The use of the device to close a laceration or incision will be discussed in greater detail below, however, a brief orientation at this stage in the discussion is helpful. In use, the adhesive-backed anchoring member of the first component of the device is applied to the skin of the animal or human patient adjacent to the laceration or incision to be closed. The wound edge of the first component is placed very near to the edge of the laceration or incision, but not so close as to introduce adhesive from the first component anchoring member into the open area of the laceration or incision. The one or more elongated connectors extend from the wound edge of the anchoring member of the first component, in a direction which is generally perpendicular to the wound edge, and extend across the area of a laceration or incision to the opposite side of the laceration.

A similar application procedure is followed for application of the second component, the procedure for the application of the second being the mirror image of the procedure for application of the first. Following application of the adhesive-backed anchoring members, the laceration is closed by either pushing anchoring members toward one another, or by pulling them together by grasping one or more elongated connectors from each component and pulling the laceration closed. Very fine adjustment can be made in the X and Y dimension ensuring laceration closure with minimal scarring. When the first and second component are positioned to the satisfaction of the physician, or other individual applying the device, the relationship of the two components is fixed by attaching the one or more elongated connectors of the first component to the anchoring member of the second component, and by attaching the one or more second elongated connectors of the second component to the anchoring member of the first component.

Adhesives

The adhesives selected for use in connection with the present disclosure must meet a number of requirements. First, adhesive which is to come into contact with the skin must be selected to minimize the potential for adverse reaction by the skin. That is, the adhesive selected should be hypoallergenic. Additionally, all adhesives, whether or not they are intended to contact the skin, must provide a secure hold for a period of time sufficient for the healing process to progress to the point where removal of the device is appropriate. An adhesive hold period of about 7-10 days is generally suitable.

Adhesive is a preferred means of attaching one or more elongated connectors to a adhesive-backed anchoring member. In one embodiment, adhesive is applied to at least a portion of the lower surface of the elongated connectors for attaching the elongated connectors of one of the two components to the applied anchoring member of the other component. Alternatively, or additionally, adhesive may be applied to a portion of the upper surfaces of the first and second adhesive-backed anchoring members. Release liners are used to protect applied adhesives prior to application of the device.

The elongated connectors have two parts or portions, an attached portion and a bridging portion. The attached portion of the elongated connectors, as the name indicates, is that portion which is attached to the anchoring member of the opposing component following application of the device. The bridging portion is the portion of the elongated connector or members which spans the over-laceration area. In further refined embodiments, the lower surface of the bridging portion contains less adhesive than the attached portion. In preferred embodiments, the entire bridging portion of the one or more elongated connectors is free of adhesive or, alternately, have adhesive but this is blocked with another film (kill layer) to render the adhesive in the bridging portion nonfunctional.

Elongated Connectors

As mentioned above, the dimension of the elongated connectors is strap-like in that their width is substantially greater than their thickness. In light of the fact that the point of attachment between the first and second elongated components is between the underside of attached portions of elongated connectors with the upper surface of attached elongated components, maximizing the area of contact will result in a more secure closure of the device because the area of adhesive contact is maximized. Thus, from the standpoint of security of closure, wider attached portions are preferred. However, as the width of all the elongated connectors is increased, the distance between elongated connectors necessarily is decreased. It is extremely important that there be enough distance between adjacent elongated connectors to facilitate fine adjustment of the device as the second anchoring member is being positioned, and after the two anchoring members are positioned, but prior to fixing their relationship by attaching elongated connectors to anchoring members.

As was stated in U.S. Pat. No. 6,329,564, the disclosure of which is incorporated herein by reference: There is no absolute minimum which can be stated with respect to spacing between elongated connectors. Preferred ranges are probably best stated as a percentage of device length (i.e., the dimension of the device generally parallel the laceration or incision). For example, a spacing of between about 5% to about 10% of the bandage length is an example of an appropriate range.

This spacing provides substantial adhesive contact between attached portions of elongated connectors with anchoring members, as well as sufficient spacing for fine adjustment of both before and following the attachment of the second anchoring member. Fine adjustment made after the attachment of the second anchoring member is generally a concern after the laceration has been closed and just prior to attachment of elongated connectors to an adhesive-backed anchoring member. At this stage in the application process, the bridging portions of the one or more first elongated connectors and the bridging portions of the one or more second elongated connectors are aligned with one another over the closed laceration or incision. In a preferred embodiment of the present disclosure, the average width of the bridging portions is less than the average width of the attached portions of the elongated connectors. Average width is determined by measuring from the outer perimeters of the bridging portions and the outer perimeters of the attached portions.

This difference in width in the bridging portion relative to the attached portion affords advantages over prior art devices in which the width of elongated connectors was substantially constant along their length. Consider, for example, a prior art device designed for maximum security. In such a device, the elongated connectors would be placed as close as possible, while still providing for a minimum acceptable degree of adjustment range. If the bridging area were narrowed in such a device, the net effect would be an increase in exposed area over the laceration (which is desirable for application of medicines, removal of exudates, etc), as well as an increase in the range of adjustment (narrowing the width of the elongated connectors in the bridging portion effectively increases the distance between adjacent bridging portions).

Considering the same prior art device discussed in the preceding paragraph, holding the width of bridging portion constant, while increasing the width of the attached portions provides for greater security as the area of adhesive contact is effectively increased. It will be recognized by one skilled in the art that hybrid configurations (i.e., devices having narrowed bridging portions and widened attached portions relative to prior art, uniform width devices) represent important embodiments of the present disclosure.

Elongated connectors may be viewed as strap-like in their dimensions. In preferred embodiments, a portion of the elongated connectors is cut away to increase the unobstructed surface area over the wound or incision. This tends to facilitate drainage of exudates and application of medication. This cut-out is best produced during the die cut process. U.S. Pat. No. 6,329,564, the disclosure of which is incorporated herein by reference, depicts cut-outs, for example, in FIG. 3. The shape of the cut-out is not critical. What is important is that the structural integrity of the elongated connectors is not compromised by the introduction of the cut-outs.

Pulling Elements

Preferred embodiments of the present disclosure include pulling elements which are attached to elongated connectors, or to extensions of elongated connectors. Extensions of elongated connectors could themselves be considered to be pulling elements in embodiments in which only one elongated connector is associated with a component. By definition, the attached portion of an elongated connector attaches to the anchoring member of another component. Extensions of an elongated connector extend the length of the elongated connector for ease of application, and are generally removed following the application process. Perforations or scoring are preferably provided to facilitate their removal. For embodiments in which the number of elongated connectors associated with a component is greater than one, a pulling element is useful for joining the elongated connectors or extensions of elongated connectors to enable a user to easily apply a pulling force to more than one connecting member.

Removal of the pulling elements minimizes the footprint of the applied two-component device. This decrease in the overall size of the device reduces the chance that a portion of the bandage may be caught, for example, on clothing or a pillow. Such an occurrence could tend to pull the applied device away from the skin thereby causing the wound or incision to open. Minimizing the overall footprint of the applied device also tends to provide for a more comfortable fit.

Eversion Edges

In preferred embodiments, the wound edges of the first and second adhesive-backed anchoring members, are adapted to evert (or raise) skin edges to promote wound healing. It is known in the art that everting, raising or mounding of the skin edges at the wound or incision site prevents wound inversion. One way in which this can be accomplished is to provide a bend at the wound edge. The bend may be angled or arcuate. The adhesive on the lower portion of the adhesive-backed anchoring members is also applied to the wound edge portion. When attached to the skin this eversion edge tends to lift the edges of the skin at the point of closure contact, thereby promoting wound or incision healing.

Coding

To minimize confusion for new users of the device of the present disclosure, the pulling elements and anchoring members may be coded to enable user distinction. Thus, for example, the coding may comprise an observable geometric distinction between the shape of the pulling elements and the shape of the adhesive-backed anchoring members. In another embodiment, such coding may comprise printed indicia to enable user distinction between the components. Colors may also be used to provide this distinguishing function.

Lateral Translation Element

In instances of the present disclosure, both the first and second elongated components of the two-component device of the present disclosure comprise one or more first elongated connectors attached to a single first pulling element. In other instances, one of the first or the second elongated components, but not both, comprise one or more lateral translation elements. In these embodiments, one of the first or the second elongated components comprises one or more lateral translation elements, and the other elongated component comprises a plurality of lateral translation elements, each comprising one or more elongated connectors attached to a single pulling element.

Each lateral translation element is selected from the group consisting of: a) a single elongated connector and a single pulling element; and b) a plurality of elongated connectors and a single pulling element.

Release Liners

The adhesive-backed surfaces of the device of the present disclosure are protected (e.g., from contamination and oxidation) by the application of release liners during the manufacturing process. In some instances, multiple release liners, or release liner systems may be used to protect a single, uninterrupted, adhesive-backed surface. Consider, for example, the anchoring members of the disclosed device. In order to precisely attach the wound edge of an anchoring member adjacent a laceration or incision to be closed, it is preferable to hold the anchoring member with one hand leaving the other hand free to manipulate the laceration or incision area. Thus, a plurality of release liners on each anchoring member is preferred. In preferred embodiments, a first release liner, which protects the wound edge, is removed first during the application process. In this way, a portion of the wound edge can be adhered to the skin while leaving a protected portion of the anchoring member which can be held (e.g., in a gloved hand) without the device adhering to the fingers of the user. Once the wound edge has been applied, the second release liner can be removed to fully secure the anchoring member. Preferred release liner stock includes paper, cardboard or polymeric sheet stock. The use of a plurality of release liners in connection with the adhesive associated with the elongated connectors is less important as extensions of the elongated connectors and pulling elements are provided "adhesive-free" in preferred embodiments. To minimize confusion for new users of the device of the present disclosure, the release liners may also be coded. Release liner colors or printed indicia on the release liner are examples of coding enabling a user to readily identify the order of release liner removal.

As discussed above, the film or sheet stock used to manufacture the first and second components of the device of the present disclosure can be, and preferably are, extremely thin. When applying an anchoring member produced from such thin stock next to a laceration or incision, it is easy to imagine difficulties associated with wrinkling and overlapping of edges, inadvertent or incorrectly positioned initial contact, etc. The release liners employed in connection with the device can provide substantial aid in working with the device, particularly a device produced from thin sheet stock, if properly selected. For example, if two release liners are used to protect the adhesive-backed surface of an anchoring member, the characteristics of the release liner protecting the wound edge of the anchoring member is far less important than the characteristics of the later-removed, second release liner protecting the adhesive-backed anchoring member. If, for example, a semi-rigid second release liner is employed, this will enable more precise placement of the wound edge of the adhesive-backed anchoring member.

Alternative Stock

The embodiments of the device discussed above comprise first and second components which are monolithic in nature. That is, the first component (which includes an anchoring member and one or more elongated connectors) is produced from a single sheet of stock material without joints or seams. The same statement applies to the second component. In an alternative embodiment, the first and second components are not monolithic in nature. This alternative embodiment is based on the recognition that the desired physical properties of the anchoring members and the elongated connectors are not, in every instance, identical. For example, a degree of elasticity is a desirable feature in an anchoring member when applied, for example, to an area such as a joint. An anchoring member produced from a film having a degree of elasticity is less likely to release prematurely than an anchoring member produced from a substantially inelastic material when applied to such an area. Elasticity is a property to be avoided when producing elongated connectors. Any stretching of elongated connectors is to be avoided as this will tend to allow premature opening of a laceration or incision.

In embodiments in which the first and second components are not monolithic, anchoring members may be produced from stock having a degree of elasticity. Elongated connectors are produced separately from stock which is substantially inelastic. One or more first elongated connectors are then attached (e.g., with adhesive) to a first anchoring member to produce a first component. A second component is similarly constructed. As discussed elsewhere, a wound edge bar may be attached to reinforce the wound edge, particularly in embodiments wherein the sheet stock employed has a degree of elasticity.

It is not a requirement that elongated connectors and anchoring members of non-monolithic components be produced from different stock material. It may be desirable, for example, to create an overlap in a portion of the elongated connectors (e.g., the bridging portion) in order to provide for additional strength. Thus, double-thickness in the bridging area may be provided by producing a monolithic anchoring member including a portion of connecting member. A separately produced elongated connector is then attached, in an overlapping manner, to the monolithic anchoring member. This creates a first component which is double-thick in the bridging portion for additional strength and further eliminates stretching.

Reinforcing Elements

It may be desirable to reinforce the wound edge portion of the anchoring member with another layer of less flexible stock. This "wound edge bar" would provide better translation of the force applied by the elongated connectors uniformly along the entire wound edge. Similarly, it may be desirable to reinforce the optional pulling element, or a portion thereof, with another layer of less flexible stock. This "pull bar" would be useful in applying uniform tension from the pulling element to all elongated connectors, as the device is positioned for closure. This feature would become more important in embodiments of the device intended to close long lacerations or incisions where there might be up to four or more elongated connectors to be pulled and secured to each adhesive-backed anchoring member.

Elastic Tension Indicators

The bandage of the present disclosure may optionally include an elastic tension indicator element. The purpose of the tension indicator element is to provide a visual indication that a desired tension has been reached while applying the bandage. For example, materials are known in the art which change color when a predetermined tension is applied. Similarly, other graphic representations may be used for this purpose. For example, a rectangular graphic representation may be applied to an elastic tension indicator element. As this tension indicator is stretched, the graphic representation of the rectangle stretches. This element may be designed such that the desired tension is indicated when the original rectangular representation is stretched to the point where it closely approximates a geometric square.

It is desirable that this elastic tension indicator element be removable with the pulling elements following application of the bandage. At a minimum, the elastic tension indicator element should be positioned in the bandage such that when the bandage is applied, it is not possible for the elastic element to continue to stretch and release the desired tension previously established.

Transdermal Drug Delivery

The two-component device of the present disclosure can be optionally adapted for transdermal drug delivery. As is known in the art, a drug is deliverable transdermally through the skin. For such an application, a drug-containing patch is secured to at least one of the adhesive-backed anchoring members in such a way that the drug can be delivered through the skin. Given the fact that there will be no adhesive contact between the skin and the adhesive-backed anchoring member in the area of the drug delivery patch, it may be necessary to increase the size of the flat flexible component to secure the bandage in such a transdermal drug delivery embodiment. Transdermal drug delivery is well known in the art and a review of the background is not necessary to enable one of skill in the art to make and use the presently disclosure.

Embedded Infection Indicators

The use of embedded infection indicators represents a relatively new technology that can be incorporated to provide for a wound closure device that can, for example, change color as an indication of the presence of unwanted bacteria. One technology utilizes the release of a fluorescent dye from nanocapsules, the release being triggered by toxins secreted by the unwanted bacteria.

Methods of Use

The present disclosure also relates to methods for closing a laceration or incision using a device of the type described above. Such methods include the steps of applying the anchoring member of a first and second component on opposing sides of a laceration or incision to be closed. The laceration is then closed by the user either by pushing the edges of the laceration together by manipulating the skin in the area of the adhesive-backed anchoring members, by pulling the laceration closed using lateral translation elements, or by some combination thereof. Once the laceration is closed, the position of the first and second component relative to each other is fixed by attaching the elongated connectors to the adhesive-backed anchoring members.

The subject disclosure relates to improvements and modifications in polymeric films that comprise the adhesive-backed anchoring members of the two-component medical devices. More particularly, instances of the present disclosure include a first and second adhesive-backed anchoring member characterized by the presence of one or more discontinuities in the polymeric film allowing for the release of sweat from beneath the first and second adhesive-backed anchoring members. The use of an inherently breathable polymeric film (i.e., a polymeric film, that without any mechanical manipulation, allows for the exchange of air with the skin beneath the first and second adhesive-backed anchoring members) for the production of the first and second adhesive-backed anchoring members does not allow for the release of sweat.

Certain mechanical manipulation of an inherently breathable polymeric film that does not allow for the release of sweat will permit sweat to pass from the skin beneath the wound closure device. The same can be said for mechanical manipulation of a polymeric film that is not inherently breathable.

The introduction of discontinuities that do allow for the release of sweat from beneath the first and second adhesive-backed anchoring members addresses the problem of adhesion loss. There is variability in the size, number and distribution of active sweat glands in humans. For example, according to one expert estimate, the palm of the hand has about 370 sweat glands per $cm^2$. By comparison, the back of the hand has about 200; the forehead has about 175; the breast, abdomen and forearm have about 155; and the leg and back have about 60-80 (all expressed in sweat glands per $cm^2$). Given this sweat gland distribution pattern, one skilled in the art will recognize that discontinuities should be introduced broadly, across the area of the adhesive-backed anchoring members, to be most effective in addressing the problem of adhesion loss.

Discontinuities can be introduced into the polymeric material used to produce the first and second adhesive-backed anchoring members in a variety of ways. It is not a requirement that all discontinuities introduced into a particular adhesive-backed anchoring member be homogenous or uniform. Die cutting technology is a preferred method for the introduction of discontinuities. Die cutting is a process involving the use of a die to shear a web or webs of low-strength materials such as polymeric sheet materials. For example, a needle or pin die could be used to introduces hundreds, or even thousands of small, round discontinuities into the first and second adhesive-backed anchoring members through a perforation process. Perforation, as used herein, refers to a process wherein a discrete piercing element, such as a pin in an array of pins assembled on a die, penetrates a material leaving no excess material on either side (e.g., entry or exit side). Whether penetration by a particular piercing element leaves excess material on one side or another (e.g., deformation of material on the exit side) depends not solely on the piercing element, but also the material being pierced (in this case a polymeric sheet material). For example, a larger gauge piercing element, the size of a small nail, for example, may create exit deformation in some polymeric sheet stocks that would not be useful for the introduction of discontinuities consistent with the present disclosure. The shape of a piercing element need not be round. There are no geometric restrictions on the shape of a piercing element.

For the introduction of larger discontinuities, like those produced by piercing a polymeric material with a small nail, a punch process may be more appropriate. A punch, as used herein, is contrasted from a perforation by the requirement that material is removed in a punch process. For example, a punch die of a particular diameter would punch, or remove, a chad from the polymeric material. Such loose chads are removed in a variety of ways in a die cutting process including, for example, inclusion of an adhesive web to capture cut chads, or a vacuum process. Punches will tend to be visible to a user inspecting the applied two-component medical device whereas slits, slices and perforations are practically invisible to the unaided eye.

In addition to perforation or punching, as described above, cutting (e.g., die cutting) can be used to introduce one or more slits or slices into the adhesive-backed anchoring members. Again, in view of the sweat gland distribution discussed above, a plurality of slits will be preferred.

One of skill in the art will recognize that a certain amount of routine experimentation may be required to optimize discontinuity size, shape and distribution. Certainly larger gauge perforations, punches or slits will allow for the transfer of sweat from the skin beneath the wound closure device. Certain smaller gauge perforations, produced for example using a pin die as discussed above, may allow for vapor transfer but not sweat transfer. It is a matter of routine experimentation to determine discontinuity parameters that will allow for sweat transfer. Optimal discontinuity design for one specific polymer sheet backed with one specific adhesive, may not work well using a different polymer sheet and/or different adhesive. A particularly soft or gummy adhesive, for example, may function in a self-healing role by flowing in to fill perforations when such perforations are introduced with a particularly small diameter piercing element.

It will also be recognized by one of skill in the art that punch-type discontinuities will tend to remove skin contact surface area (and adhesive) from an adhesive-backed anchoring member. For this reason, larger punch-type discontinuities (e.g., paper punch size discontinuities, or larger) are not favored, at least for applications requiring high adhesion characteristics.

For a variety of reasons, slits or slices introduced into the adhesive-backed anchoring members are preferred. For one, like perforations, slits or slices do not remove material from the adhesive-backed anchoring members and, therefore, the adhesive-backed anchoring members retain their full surface area and adhesive content following the introduction of the slits or slices. Slits or slices can be straight or curvilinear and the slits or slices can be relatively long (e.g. running the length or width of an adhesive-backed anchoring member) or generally short in length. Furthermore, under flexion, a slit or slice will tend to open up. This tendency serves at least two purposes that represent advantages in the context of a two-component wound closure device. First, the "opening up" of a slit or slice under flexion enables relative unimpeded transfer of sweat from the surface of the skin beneath the adhesive-backed anchoring member to the external environment. Second, the "opening up" of the slit or slice tends to allow the adhesive-backed surfaces adjacent to the slit or slice to remain in good adherence with the skin. The present of the slit or slice tends to reduce peel or shear forces that tend to result in poor adherence characteristics. When introduced, in embodiments of slices are relatively long the effect can be the creation of a plurality of adhering subdomains in the adhesive-backed anchoring member.

In preferred instances, slits are introduced into each adhesive-backed anchoring members in a direction generally perpendicular to the wound edge of the adhesive-backed anchoring member. The slits are positioned so that they will fall between elongated connectors in an applied device. Slits oriented in this way tend to allow a particular adhesive-backed anchoring member to be viewed as a unit having a number of adhering subdomains, with the adhering subdomains being divided by the introduced slits. The adhered two-component device opens in an accordion-like manner under flexion. In instances of the two-component device disclosed, the adhering subdomains can actually separate from one another over time thereby creating independent subdomains.

Mechanical manipulation of the type described above can provide for "elastic-like" properties in non-elastic polymers. Although the mechanical manipulation does not change the non-elastic characteristic of the particular polymer, the introduction of voids or discontinuities can allow for movement in dimensions where no movement would be possible absent the voids or discontinuities.

Figure 1A:
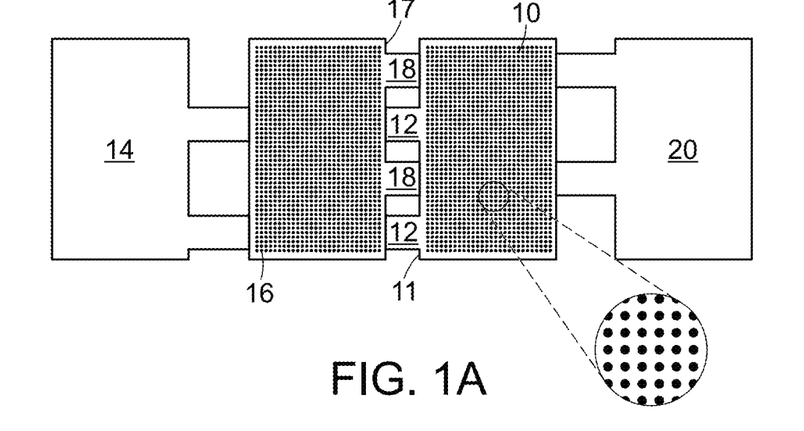
FIG. 1A is a bottom view of an interlaced wound closure device showing perforation-type discontinuities in the adhesive-backed anchoring members.
Figure 1B:
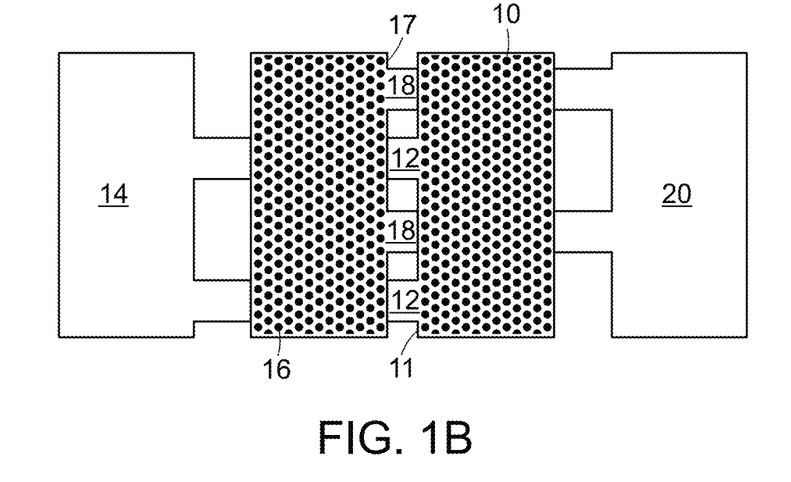
FIG. 1B is a bottom view of an interlaced wound closure device showing punch-type discontinuities in the adhesive-backed anchoring members.
Figure 1C:
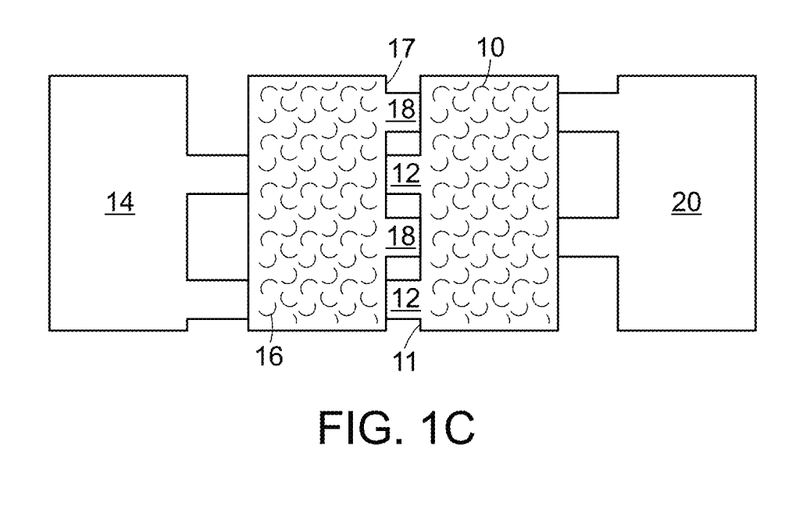
FIG. 1C is a bottom view of an interlaced wound closure device showing curvilinear discontinuities in the adhesive-backed anchoring members.

Having described specific instances of discontinuities in connection with the present disclosure, reference will now be made to drawings. FIGS. 1A, 1B and 1C are bottom projection views of an interlaced wound closure device of the present disclosure showing only structural film elements without release liners. Common elements depicted in the three Figures include first adhesive-backed anchoring member 10 having a wound edge 11, first elongated connectors 12, first pulling element 14, second adhesive-backed anchoring member 16 having a wound edge 17, second elongated connectors 18 and second pulling element 20.

Each of FIGS. 1A, 1B and 1C show a homogenous discontinuity pattern. In other words, each discontinuity in FIG. 1A is substantially identical with all others. The same can be said for FIGS. 1B and 1C. As indicated previously, homogeneity of discontinuities on a particular adhesive-backed anchoring member, or a particular two component medical device, is not a requirement.

FIG. 1A shows over 1,000 specific discontinuities in first adhesive-backed anchoring member 10 and second adhesive-backed anchoring member 16. Each discontinuity is generally small and circular and a preferred method of introducing such discontinuities would be perforation through a needle or pin die cutting process. As mentioned previously, some routine experimentation will be required to optimize perforation in connection with a particular combination of polymeric sheet material and an adhesive to be used to secure the processed polymeric sheet material (in the form of an adhesive-backed anchoring member) to the skin.

FIG. 1B shows over 750 specific discontinuities in first adhesive-backed anchoring member 10 and second adhesive-backed anchoring member 16. Each discontinuity is circular and larger than that shown in FIG. 1A. Because of the somewhat larger size of the discontinuity, a punch process would likely be the preferred method of introducing such discontinuities through a punch die cutting process. Punch processing will produce a chad which must be captured and removed during the manufacturing process. The exact transition from pin or needle die processing to punch die processing cannot be expressed in terms of a precise dimension as polymer sheet type, and adhesive type are variables that must be taken into account.

FIG. 1C shows scores of specific "slit" or "slice" discontinuities in first adhesive-backed anchoring member 10 and second adhesive-backed anchoring member 16. Each discontinuity is curvilinear and no material is removed from adhesive-backed anchoring member 10 and second adhesive-backed anchoring member 16 during the process of introducing the "slit" or "slice" discontinuities. Such "slits" or "slices" are preferably introduced using an appropriately designed cutting die. An advantage of the curvilinear slice, or any slice for that matter, is that it does not require particulate or chad removal.

Figure 2:
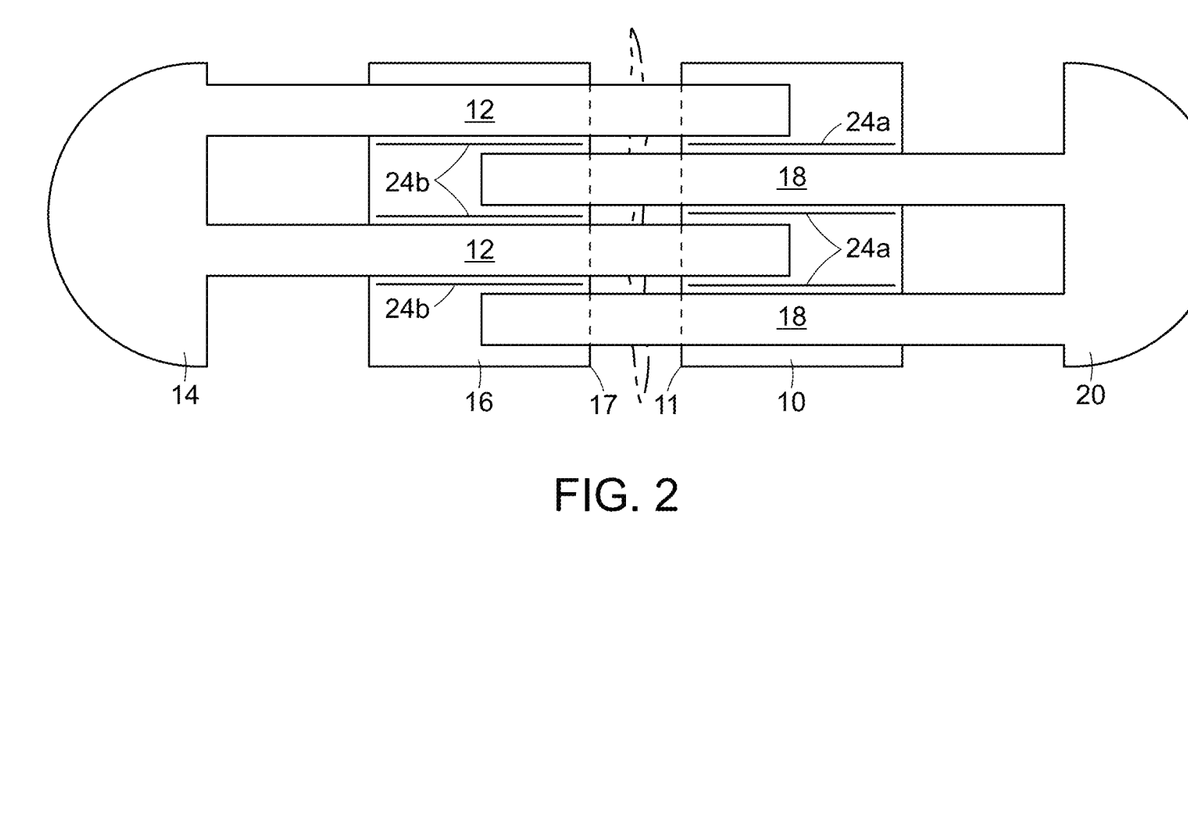
FIG. 2 is a top view of an interlaced wound closure device showing slit-type or slice-type discontinuities in the adhesive-backed anchoring members.

FIG. 2 is a top projection view of an interlaced wound closure device of the present disclosure showing only structural film elements without release liners. Common elements depicted in the three Figures include first adhesive-backed anchoring member 10 having a wound edge 11, first elongated connectors 12, first pulling element 14, second adhesive-backed anchoring member 16 having a wound edge 17, second elongated connectors 18 and second pulling element 20.

The discontinuities shown in FIG. 2 are "slits" or "slices". From the top view, it can be clearly seen that the slits 24*a* introduced into first adhesive-backed anchoring member 10 in the instance shown will fall between second elongated connectors 18 in an applied two component device. Similarly, slits 24*b* introduced into second adhesive-backed anchoring member 16 in the instance shown will fall between first elongated connectors 12 in an applied two component device. While the length of the slits can be variable, as can the number of slits between elongated connectors in an attached device, it is preferred that one end of the slits 24*a* on first adhesive-backed anchoring member 10 closely approach wound edge 11. It is also preferred that the other end of the slits 24*a* on first adhesive-backed anchoring member 10 closely approach the edge generally opposite wound edge 11. Similarly it is preferred that one end of the slits 24*b* on second adhesive-backed anchoring member 16 closely approach wound edge 17. It is also preferred that the other end of the slits 24*b* on second adhesive-backed anchoring member 16 closely approach the edge generally opposite wound edge 17.

The reason for the stated preference as to the length of the slits will be clear following a review of the Exemplification section which follows. In brief, the data presented in the Exemplification section supports the proposition that the combined shear strength of two individual segments of polymeric material exceeds that of an otherwise identical single polymeric segment construct having equal area as compared to the two individual segments combined. The effective separation of adhesive-backed anchoring member 10 into four individual segments (also referred to as adhering subdomains), as shown in FIG. 2 will similarly provide for enhanced shear strength as compared to first adhesive-backed anchoring member 10, lacking the slit discontinuities. It will be recognized that the comments made above in connection with the introduction of slits into first adhesive-backed anchoring member 10 apply equally to slitted instances of second adhesive-backed anchoring member 16.

It was stated above that it is preferred that one end of the slits 24*a* on first adhesive-backed anchoring member 10 closely approach wound edge 11. The integrity of wound edge 11 must be maintained during the application process. Therefore, prior to application, the slits 24*a* on first adhesive-backed anchoring member 10 should not extend all the way to wound edge 11, thereby severing wound edge 11. In another instance of the present disclosure, slits 24a on first adhesive-backed anchoring member 10 may terminate near wound edge 11, and a perforations may be introduced extending the slits 24a all the way to wound edge 11. The perforations will not separate during the application process and the integrity of the wound edge will be maintained. However, in the weeks following application, due to flexion and stretching, the perforations may break at the wound edge thereby allowing adhering subdomains of the first adhesive-backed anchoring member 10 to operate more independently. The disclosure regarding slits 24a applies equally to slits 24b.

Referring again to slits 24a in first adhesive-backed anchoring member 10 in FIG. 2, at the edge of the first adhesive-backed anchoring member 10 generally opposite wound edge 11, slits may be extended to the edge by perforation, as discussed above in connection with perforations approaching the wound edge. Furthermore, the integrity of the edge generally opposite wound edge 11, is not as critical as the integrity of wound edge 11. Using no more than routine experimentation, it may be determined that slits may be introduced in the manufacturing process that actually sever the edge of the first adhesive-backed anchoring member 10 generally opposite wound edge 11. Again, comments relating to extension of slits toward edges apply equally to second adhesive-backed anchoring member 16.

EXEMPLIFICATION

Preferred polymeric sheet materials were applied to a substrate material and subjected to cyclic 10% stretching to simulate use in vivo. Following cyclic stretching, the adhered polymeric materials were subjected to shear testing to evaluate adherence.

The substrate material utilized to simulate skin was silicone rubber (30 A durometer high temp super-soft silicone rubber sheet, McMaster-Carr Inc., IL). Cyclic stretching involved adhering a 3 inch×0.75 inch sample of polymeric sheet material onto a 9 inch×3 inch silicone rubber strip. On two separate 9 inch×3 inch silicon rubber strips, an individual first strip of the same polymeric material cut to 1.5 inch×0.75 inch dimensions was applied, and an individual second strip of the same polymeric material cut to 1.5 inch×0.75 inch dimensions was applied. The combined surface area of the two 1.5 inch×0.75 inch strips was equivalent to the single 3 inch×0.75 inch strip. The adhesives used in all instances described were identical.

Each of the silicone strips, with adhered polymeric material, was secured only cylindrical holders attached to an MTS machine (MTS Systems Corp., Eden Prairie, MN) via double sided tape (0.75 inch double sided tape, Intertape Polymer Group Inc., Montreal, Canada), such that the free length of the silicone strip between the holders was 9 inches. MTS Systems Corp. is an industry leading testing and sensing solution company and a number of their products (including MTS model 569326-05, capacity 100N) were utilized in the work described in this section. The silicone strip, together with the adhered polymeric material, was then subjected to repeated tensile strain of 0-10% (10%×9 inches=0.9 inches of displacement) at 1 Hz frequency for 24 hours to simulate roughly two weeks of in vivo use. This was based on an assumption of approximately 2 million cycles of joint motion per year. Images of the samples were taken before and after testing to visually capture the extent of the adherence of the material following approximately 86,200 cycles (24 hours at 1 Hz) of stretching.

Following cyclic stretching, the silicone rubber substrate strips were fixed to an MTS machine base using double sided tape. Force was then applied to the polymeric material adhered to the silicone rubber strips, in the plane of application, until the polymeric material fractured. Table 1 below summarizes the peak and average forces recorded during the shear testing. The polymeric material used in the testing was coded 3604A, and was polyurethane (7 mil thickness).

TABLE 1

|  | Dimension of Material 3604A (inches) | Max Shear Force (Newtons) | Average Shear Force (Newtons) |
| --- | --- | --- | --- |
| Full Strip | 3 × 0.75 | 35.6 | 21.8 |
| Half Strip 1 | 1.5 × 0.75 | 27.7 | 20.1 |
| Half Strip 2 | 1.5 × 0.75 | 22.5 | 16.8 |

As previously stated, the shear tests were performed following cyclic stretching. Results determined in connection with the full strip (3 inch×0.75 inch) showed a maximum shear strength of 35.6N. Individual half strip 1 (1.5 inch×0.75 inch) showed a maximum shear strength of 27.7N and individual half strip 2 (1.5 inch×0.75 inch) showed a maximum shear strength of 22.5N. Therefore, with regard to attachment strength under shear loading, although the individual half strip segments had lower adhesion strength that the single full strip, the combined shear strength of the two individual segments exceeded that of the single segment construct.

The invention claimed is:

1. A two-component medical device for closing a wound or incision, comprising:
 a) a first component comprising:
  i) a first adhesive-backed anchoring member for adhering to skin of a patient, the first adhesive-backed anchoring member having a wound edge and an edge opposite the wound edge,
  wherein the first adhesive-backed anchoring member is produced from an adhesive-backed polymeric film sheet and comprises a first continuous, without interruption, linear slit having:
   a first terminus spaced apart from and positioned closer to the wound edge than it is to the edge opposite the wound edge, and
   a second terminus spaced apart from and positioned closer to the edge opposite the wound edge than it is to the wound edge,
  wherein the first continuous, without interruption, linear slit of the first adhesive-backed anchoring member is characterized by penetrating both the polymeric film sheet and the adhesive-backing of the first adhesive-backed anchoring member,
  wherein positioning of the first terminus and the second terminus with respect to the wound edge and the edge opposite the wound edge creates respective breakable points in the wound edge and the edge opposite the wound edge, the breakable points being susceptible to breakage under flexion and stretching forces when the first adhesive-backed anchoring member is adhered to skin of the patient,
  ii) one or more first elongated connectors extending from the wound edge of the first adhesive-backed anchoring member; and
  iii) one or more first pulling elements joined to the one or more first elongated connectors and adapted for translation of the first adhesive-backed anchoring member toward the wound or incision;
b) a second component comprising:
i) a second adhesive-backed anchoring member for adhering to skin of the patient, the second adhesive-backed anchoring member having a wound edge and an edge opposite the wound edge,
wherein the second adhesive-backed anchoring member is produced from an adhesive-backed polymeric film sheet and comprises a first continuous, without interruption, linear slit having:
a first terminus spaced apart from and positioned closer to the wound edge than it is to the edge opposite the wound edge, and
a second terminus spaced apart from and positioned closer to the edge opposite the wound edge than it is to the wound edge,
wherein the first continuous, without interruption, linear slit of the second adhesive-backed anchoring member is characterized by penetrating both the polymeric film sheet and the adhesive-backing of the second adhesive-backed anchoring member,
wherein positioning of the first terminus and the second terminus with respect to the wound edge and the edge opposite the wound edge creates respective breakable points in the wound edge and the edge opposite the wound edge, the breakable points being susceptible to breakage under flexion and stress forces when the second adhesive-backed anchoring member is adhered to skin of the patient;
ii) one or more second elongated connectors extending from the wound edge of the second adhesive-backed anchoring member; and
iii) one or more second pulling elements joined to the one or more second elongated connectors and adapted for translation of the second adhesive-backed anchoring member toward the wound or incision;
c) one or more release liners protecting the adhesive-backed surfaces of the first adhesive-backed anchoring member and the second adhesive-backed anchoring member;
d) means for attaching the one or more first elongated connectors to the second adhesive-backed anchoring member, thereby forming an attached portion and a bridging portion for each attached first elongated connector; and
e) means for attaching the one or more second elongated connectors to the first adhesive-backed anchoring member, thereby forming an attached portion and a bridging portion for each attached second elongated connector.

2. The two-component medical device of claim 1, wherein the first continuous, without interruption, linear slit, in the first adhesive-backed anchoring member, is perpendicular to the wound edge of the first adhesive-backed anchoring member.

3. The two-component medical device of claim 2, wherein continuous adhesive-backed polymeric film sheet is positioned between the first terminus of the first continuous, without interruption, linear slit and the wound edge, of the first adhesive-backed anchoring member, along a line extending from the first continuous, without interruption, linear slit of the first adhesive-backed anchoring member.

4. The two-component medical device of claim 2, wherein continuous adhesive-backed polymeric film sheet is positioned between the second terminus of the first continuous, without interruption, linear slit and the edge opposite the wound edge, of the first adhesive-backed anchoring member, along a line extending from the first continuous, without interruption, linear slit of the first adhesive-backed anchoring member.

5. The two-component medical device of claim 1, wherein:
the first adhesive-backed anchoring member further comprises a second continuous, without interruption, linear slit; and
the first continuous, without interruption, linear slit, of the first adhesive-backed anchoring member, is oriented parallel to the second continuous, without interruption, linear slit of the first adhesive-backed anchoring member.

6. A two-component medical device for closing a wound or incision, comprising:
a) a first component comprising:
i) a first adhesive-backed anchoring member having a wound edge and an edge opposite the wound edge,
wherein the first adhesive-backed anchoring member is produced from an adhesive-backed polymeric film sheet and comprises a first continuous, without interruption, linear slit having:
a first terminus spaced apart from and positioned closer to the wound edge than it is to the edge opposite the wound edge, and
a second terminus extending through and severing the edge opposite the wound edge,
wherein the first continuous, without interruption, linear slit of the first adhesive-backed anchoring member is characterized by penetrating both the polymeric film sheet and the adhesive-backing of the first adhesive-backed anchoring member,
wherein positioning of the first terminus with respect to the wound edge creates a breakable point in the wound edge, the breakable point being susceptible to breakage under flexion and stretching forces in use,
ii) one or more first elongated connectors extending from the wound edge of the first adhesive-backed anchoring member; and
iii) one or more first pulling elements joined to the one or more first elongated connectors and adapted for translation of the first adhesive-backed anchoring member toward the wound or incision;
b) a second component comprising:
i) a second adhesive-backed anchoring member having a wound edge and an edge opposite the wound edge,
wherein the second adhesive-backed anchoring member is produced from an adhesive-backed polymeric film sheet and comprises a first continuous, without interruption, linear slit having:
a first terminus spaced apart from and positioned closer to the wound edge than it is to the edge opposite the wound edge, and
a second terminus extending through and severing the edge opposite the wound edge,
wherein the first continuous, without interruption, linear slit of the second adhesive-backed anchoring member is characterized by penetrating both the polymeric film sheet and the adhesive-backing of the second adhesive-backed anchoring member,
wherein positioning of the first terminus with respect to the wound edge creates a breakable point in the wound edge, the breakable point being susceptible to breakage under flexion and stretching forces in use;

ii) one or more second elongated connectors extending from the wound edge of the second adhesive-backed anchoring member; and iii) one or more second pulling elements joined to the one or more second elongated connectors and adapted for translation of the second adhesive-backed anchoring member toward the wound or incision;

c) one or more release liners protecting the adhesive-backed surfaces of the first adhesive-backed anchoring member and the second adhesive-backed anchoring member;

d) means for attaching the one or more first elongated connectors to the second adhesive-backed anchoring member thereby forming an attached portion and a bridging portion for each attached first elongated connector; and e) means for attaching the one or more second elongated connectors to the first adhesive-backed anchoring member thereby forming an attached portion and a bridging portion for each attached second elongated connector.

7. The two-component medical device of claim 6, wherein the first continuous, without interruption, linear slit, in the first adhesive-backed anchoring member, is perpendicular to the wound edge of the first adhesive-backed anchoring member.

8. The two-component medical device of claim 7, wherein continuous adhesive-backed polymeric film sheet is positioned between the first terminus of the first continuous, without interruption, linear slit and the wound edge, of the first adhesive-backed anchoring member, along a line extending from the first continuous, without interruption, linear slit of the first adhesive-backed anchoring member.

9. The two-component medical device of claim 6, wherein:

the first adhesive-backed anchoring member further comprises a second continuous, without interruption, linear slit; and the first continuous, without interruption, linear slit, of the first adhesive-backed anchoring member, is oriented parallel to the second continuous, without interruption, linear slit of the first adhesive-backed anchoring member.

* * * * *

UNITED STATES PATENT AND TRADEMARK OFFICE
CERTIFICATE OF CORRECTION

PATENT NO. : 12,059,324 B2  
APPLICATION NO. : 18/163088  
DATED : August 13, 2024  
INVENTOR(S) : Michael Lebner

Page 1 of 1

It is certified that error appears in the above-identified patent and that said Letters Patent is hereby corrected as shown below:

On the Title Page

Item (54) and in the Specification, Column 1, Lines 1-2, The Title "POLYMERIC FILM DISONTINUITIES IN WOUND CLOSURE DEVICE" should read "POLYMERIC FILM DISCONTINUITIES IN WOUND CLOSURE DEVICE"

Signed and Sealed this  
Fifteenth Day of October, 2024

Katherine Kelly Vidal  
*Director of the United States Patent and Trademark Office*